(12) United States Patent
Bose et al.

(10) Patent No.: US 7,507,533 B2
(45) Date of Patent: Mar. 24, 2009

(54) SYSTEMS AND METHODS OF IDENTIFYING BIOMARKERS FOR SUBSEQUENT SCREENING AND MONITORING OF DISEASES

(75) Inventors: Arijit Bose, Lexington, MA (US); Nazneen Aziz, Lexington, MA (US)

(73) Assignee: Vitrimark, Inc., Lexington, MA (US)

( * ) Notice: Subject to any disclaimer, the term of this patent is extended or adjusted under 35 U.S.C. 154(b) by 45 days.

(21) Appl. No.: 11/232,597

(22) Filed: Sep. 22, 2005

(65) Prior Publication Data
US 2006/0068373 A1 Mar. 30, 2006

Related U.S. Application Data

(60) Provisional application No. 60/612,713, filed on Sep. 24, 2004.

(51) Int. Cl.
*C12Q 1/00* (2006.01)
(52) U.S. Cl. .............................. 435/6; 435/4; 435/287.1
(58) Field of Classification Search ....................... None
See application file for complete search history.

(56) References Cited

U.S. PATENT DOCUMENTS

| | | | |
|---|---|---|---|
| 5,493,865 A * | 2/1996 | Wohlwend | .................. 62/51.1 |
| 6,642,010 B2 | 11/2003 | Love et al. | |
| 6,753,135 B2 | 6/2004 | Alters et al. | |
| 6,836,557 B2 | 12/2004 | Tamez-Pena et al. | |
| 6,906,320 B2 | 6/2005 | Sachs et al. | |
| 6,939,675 B2 | 9/2005 | Gocke et al. | |

OTHER PUBLICATIONS

Al-Moudi A et al (2004) Cryo-electron microscopy of vitreous sections. EMBO J, vol. 23, pp. 3583-3588.*
Lepault J et al (1983) Electron microscopy of frozen biological suspensions. J Microscopy, vol. 129 pt 1, pp. 89-102.*
Adrian M et al (Mar. 1984) Cryo-electron microscopy of viruses. Nature, vol. 308, pp. 32-36.*
Semmler K et al (Jun. 1998) High-pressure freezing causes structural alterations in phospholipid membranes. J Microscopy, vol. 190 pt 3, pp. 317-327.*
Collet J-P et al (Jan. 1996) Fibrinogen Dusart: electron microscopy of molecules, fibers and clots, and viscoelastic properties of clots. Biophys J, vol. 70, pp. 500-510.*
Hyatt AD et al (2001) Ultrastructure of Hendra virus and Nipah virus within cultured cells and host animals. Microbes and Infection, vol. 3, pp. 297-306.*
Batt A-M et al (1995) Manifestations of chemically induced liver damage. Clin Chem, vol. 41, No. 12, pp. 1882-1887.*
Stedman's Online Medical Dictionary, 27th Edition: definition of "serum" http://www.thomsonhc.com, accessed on the internet on Sep. 26, 2007.*
Adrian et al., *Cryo-electron Microscopy of Viruses*, Nature, vol. 308, (Mar. 1984) pp. 32-36.
Al-Amoudi et al., *Cryo-electron Microscopy of Viruses*, The EMBO Journal, vol. 23, (2004) pp. 3583-3588.
Batt et al., *Manifestations of Chemically Induced Liver Damage*, Clin. Chem., vol. 41, No. 12 (1995) pp. 1882-1887.
Collet et al., *Fibrinogen Dusart: Electron Microscopy of Molecules, Fibers and Clots, and Viscoelastic Properties of Clots*, Biophysical Journal, vol. 70, (Jan. 1996), pp. 500-510.
Dubochet et al., *Cryo-electron Microscopy of Vitrified Specimens*, Quarterly Review of Biophysics, vol. 21, No. 2 (1988) pp. 129-228.
Hyatt et al., *Ultrastructure of Hendra Virus and Nipah Virus Within Cultured Cells and Host Animals*, Microbes and Infection, vol. 3, (2001) pp. 297-306.
Lepault et al., *Electron Microscopy of Frozen Biological Suspensions*, Journal of Microscopy, vol. 29, Pt. 1, (Jan. 1983) pp. 89-102.
PCT International Search Report based on PCT/US05/34097 dated Oct. 12, 2007.
Semmler et al., *High-pressure Freezing Causes Structural Alterations in Phopholipid Model Membranes*, Journal of Microscopy, vol. 190, Pt. 3, (Jun. 1998) pp. 317-327.

* cited by examiner

*Primary Examiner*—Cecilia Tsang
*Assistant Examiner*—Amanda P Wood
(74) *Attorney, Agent, or Firm*—Chinh H. Pham; Greenberg Traurig, LLP

(57) ABSTRACT

A system for generating an image of ultrastructural biomarkers from a biological sample is provided. The system includes a grid onto which a sample to be imaged may be placed and a cryogenic reservoir into which the grid and sample may be immersed for vitrification of the sample. The system also includes a stage onto which the grid and sample may be situated for subsequent imaging in a high contrast imager to permit identification of ultrastructural biomarkers therein. A method for generating an image of ultrastructural biomarkers from a biological sample is also provided. The generated image of ultrastructural biomarkers may be used subsequently for screening and monitoring diseases, evaluating drug and therapeutic efficacy, and assessing risks associated with a drug or therapeutic candidate, among other things.

24 Claims, 3 Drawing Sheets

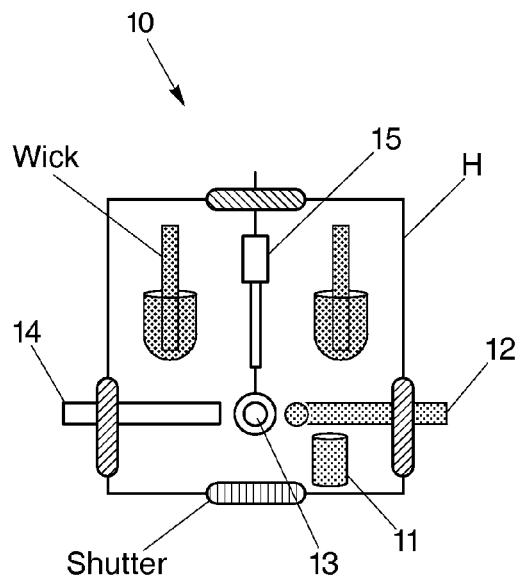
Fig. 1A
Prior Art
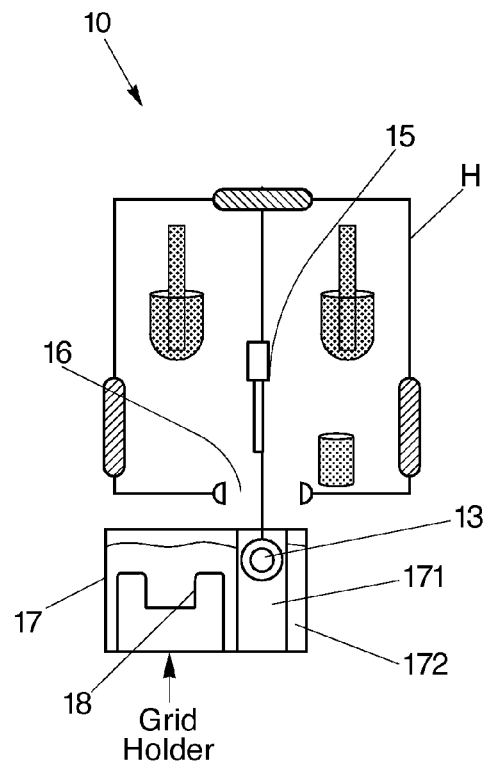
Fig. 1B
Prior Art
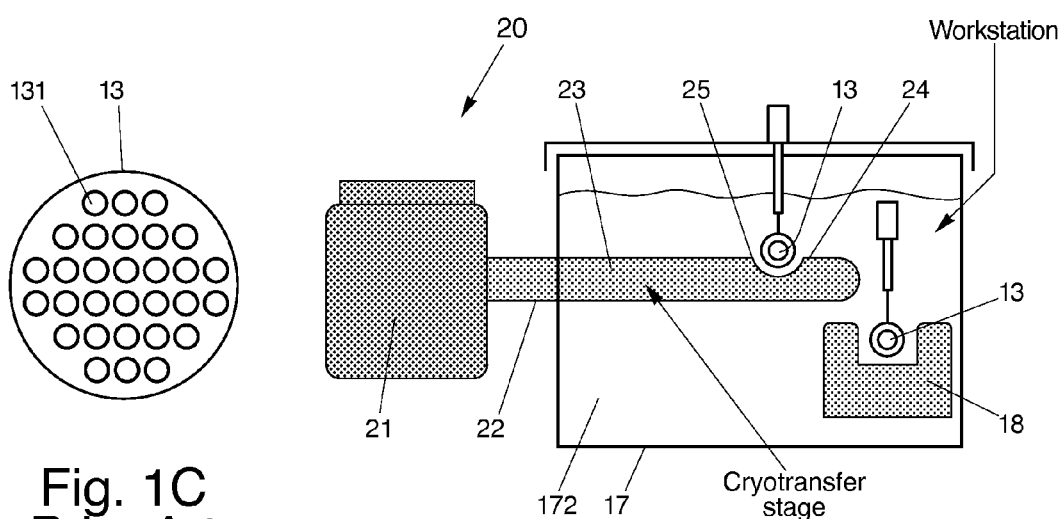
Fig. 1C
Prior Art
Fig. 2

Cryo-TEM images of a human blood serum sample. The range of observed structures include
(A) multilamellar vesicles   (B) disks   (C) compound vesicles   (D) compound disks

SYSTEMS AND METHODS OF IDENTIFYING BIOMARKERS FOR SUBSEQUENT SCREENING AND MONITORING OF DISEASES

RELATED U.S. APPLICATIONS

The present application claims priority to U.S. Provisional Application Ser. No. 60/612,713 filed Sep. 24, 2004, which application is hereby incorporated herein by reference.

TECHNICAL FIELD

This invention relates generally to imaging systems and methods, and more particularly to imaging systems and methods for identifying ultrastructural biomarkers for subsequent screening and monitoring of diseases.

BACKGROUND ART

The deepening productivity crisis in the pharmaceutical industry, the high cost to the pharmaceutical industry of introducing new drugs to the market, partly because of expenses related to Phase I, II and III clinical trials, as well as late stage failures for many drug candidates have spurred intense across-the-board activity around biomarker discovery and validation. Biomarkers, defined by the FDA as a characteristic that is objectively measured and evaluated as an indicator of normal biologic or pathogenic processes or pharmacological responses to a therapeutic intervention, are being sought actively to help make early and cost-effective "go/no-go" decisions on drugs, for patient stratification, clinical trial analysis, and finding niche markets (e.g., sub-population of patients who respond to drugs or in whom no drug-related toxicity is seen) for new drugs under development. In addition, the FDA has recently recommended that validated or investigational biomarker data be included in IND and NDA packages. These are powerful drivers for the biomarker market, whose size is estimated at $428 millions in 2005, and is growing at 20 percent per year.

The use of biomarkers is rapidly gaining momentum in the pharmaceutical industry and in the medical management of patients. Current methods for identifying biomarkers involve the use of biochemical assays for identifying "functional" biomarkers, such as genes or protein arrays or metabolite analysis. The use of biochemical assays in this context requires probing for functional alterations in genes and proteins, the need for a priori knowledge of their function, as well as extensive assay development and optimization.

While there has been an explosion of biomarker discovery efforts utilizing genomics, proteomics and metabolomics, these technologies also focus only on functional biomarkers. With many diseases, the presence of observable functional biomarkers often occurs late in the disease state. As such, preventive measures for these diseases may be ineffective when developed in connection with the management of the disease, or in early evaluation of drug efficacy.

Contributions towards understanding ultrastructural morphology have been made in recent years. Such an approach focuses on the ultra-structural differences in the biological samples that can occur much earlier in the diseased state, even before functional differences are observable. Since these target structures typically range from between about 5 nanometers (nm) and 1 micrometer, one approach to visualize them is through the use of conventional transmission electron microscopy (TEM). However, the use of conventional TEM has some critical limitations. For example (i) the high vacuum used in TEM removes solvent, leaving behind structures that are quite different from those present in the original solution, (ii) adequate contrast between the sample features and background is usually not available, necessitating the use of stains (the addition of stains, which usually are heavy metal salts, can cause dramatic changes in aggregate morphology), and (iii) the exposure of the sample to the electron beam often damages the sample.

Accordingly, it would be desirable to provide an approach that can generate substantially artifact-free images of structural biomarkers of a cell or biological sample without compromising the integrity of the biomarkers in the sample.

SUMMARY OF THE INVENTION

The present invention provides, in one embodiment, an approach through the use of cryogenic transmission electron microscopy (cryo-TEM), as well as modified freeze fracture direct imaging (M-FFDI) to identify ultra-structural biomarkers, which may subsequently be used for screening and monitoring a range of diseases. The use of cryo-TEM and M-FFDI can generate substantially artifact-free images, unlike images obtained from conventional TEM.

In accordance with one embodiment of the present invention, a system for generating an image of ultrastructural biomarkers from a biological sample is provided. The system includes a grid onto which a sample to be imaged may be placed. The grid may be perforated so that a thin film of the sample may be generated across a hole. The system also includes a cryogenic reservoir into which the perforated grid and sample may be immersed for vitrification of the sample. In an embodiment, the reservoir includes an inner chamber for accommodating a first cryogenic fluid and into which the grid and sample may be immersed, and an outer chamber situated about the first chamber for accommodating a second cryogenic fluid. The system further includes a stage, provided with a temperature substantially similar to the cryogenic reservoir, and onto which the grid and sample may be situated for subsequent imaging. The system may also be provided with a high contrast imager, such as an electron microscope, designed to receive the stage with the grid for imaging a relatively thin film region of the sample to permit identification of ultrastructural biomarkers therein.

The present invention also provides a method for generating an image of ultrastructural biomarkers from a biological sample. The method includes, in one embodiment, providing a substantially thin film of a sample to be imaged. The thin film may be generated from blotting or alternatively from sandwiching the sample between two plates. Next, the sample may be immersed in a cryogenic fluid so as to cause the sample to vitrify. This rapid vitrification allows the objects present in the sample to substantially maintain their original morphology. Once vitrified, the sample may be transferred onto a stage for placement in a high contrast imager, such as a transmission electron microscope, under positive dry pressure to minimize the risks of contamination of the sample. The transfer to the high contrast imager also includes keeping the sample at a temperature range of from about −170° C. to about −150° C. in the imager to maintain the integrity of the sample. Thereafter, an image of the thin film sample may be generated for subsequent identification of ultrastructural biomarkers. The generation of the image, in one embodiment, includes producing a substantially artifact-free image in the absence of contrasting agents.

The method for generating an image of ultrastructural biomarkers from a biological sample may be used subsequently for screening and monitoring diseases or disease susceptibility, evaluating drug or therapeutic efficacy, and assessing risks associated with a drug or therapeutic candidate, among other things. In one embodiment, a vitrified biological sample from a test subject may initially be provided. Next, an image from the vitrified sample may be generated, in a high contrast imager, for subsequent identification of ultrastructural biomarkers. Thereafter, the biomarkers from the vitrified sample may be compared to those biomarkers from a healthy subject or control population, for structural or morphological variations Subsequently, the presence of structural or morphological variations may be analyze and used as determinants or predictors for a disease, for evaluating drug or therapeutic efficacy, or assessing risks associated with a drug or therapeutic candidate.

BRIEF DESCRIPTION OF DRAWINGS

FIGS. 1A-C illustrate a system for use in preparing samples for subsequent imaging and identification of ultrastructural biomarkers.

FIG. 2 illustrates a cryotransfer station onto which a sample may be transferred for subsequent placement into a high contrast imaging device for in imaging and identifying ultrastructural biomarkers.

DESCRIPTION OF SPECIFIC EMBODIMENTS

Figure 3:
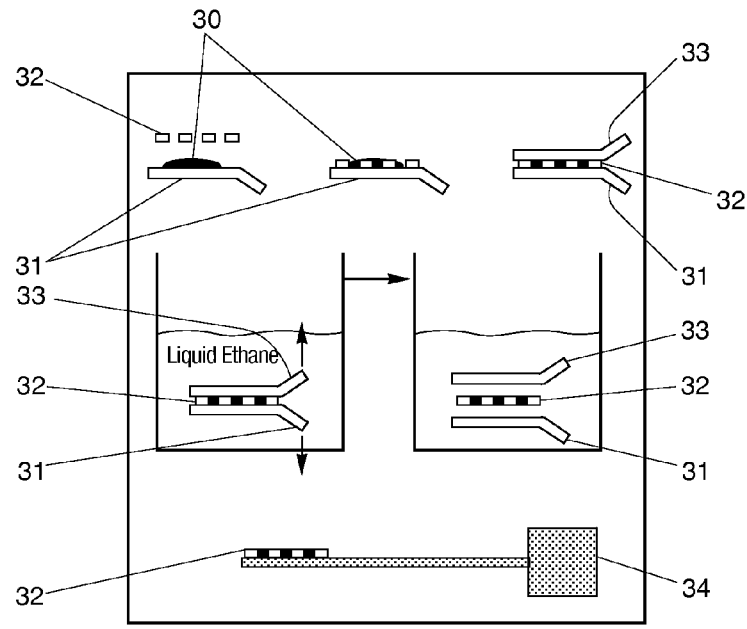
FIG. 3 illustrates schematically another method for preparing samples for subsequent imaging and identification of ultrastructural biomarkers, in accordance with an embodiment of the present invention.

The present invention provides, in one embodiment, a method for identifying ultrastructural biomarkers through the use of cryogenic transmission electron microscopy (cryo-TEM), or modified freeze fracture direct imaging (M-FFDI). In particular, the combination of cryogenic vitrification of biological samples and subsequent high contrast imaging of the samples, can preferably generate substantially artifact-free images, unlike those images obtained from the use conventional TEM alone. As such, the ability to visualize 'soft' structures that range, for instance, from between about 5 nanometers (nm) and about 500 nm, makes these artifact-free imaging techniques ideally suited for high resolution imaging of biomolecular aggregates, such as proteins, viruses and cellular organelles in their native hydrated states for ultrastructural analysis. Moreover, the data obtained by cryo-TEM or M-FFDI can complement atomic level information from, for instance, X-ray diffraction (where crystals of the sample have to be produced before identification—these crystals do not represent the true hydrated configuration in solution) and NMR, as well as micron level information from light microscopy for biomarker identification.

Cryo-TEM Technique:

1. The Controlled Environmental Vitrification System

Referring now to FIGS. 1A-C, there is illustrated a Controlled Environmental Vitrification System (CEVS)10, such as that available from The Department of Chemical Engineering & Material Sciences at the University of Minnesota, for use in the preparation of samples for subsequent ultrastructural biomarker identification. In general, the CEVS 10 includes a housing H equipped with temperature and humidity control. The CEVS 10 also includes a vial 11, within which a volume of sample may be stored. The sample within the vial 11, in one embodiment, may be thermally equilibrated relative to the interior of housing H. To extract an amount of the sample from the vial 11, a pipette 12 may be provided adjacent to the vial 11. The CEVS 10 may also include a grid 13 onto which the extracted sample may be deposited from the pipette 12. The grid 13, in one embodiment, may be a perforated disc with holes 131 that are sufficiently spaced to support the deposited sample. In an embodiment, the grid 13 may be a specially prepared holey carbon grid that is approximately 3 millimeters (mm) in diameter, if circular in shape. Of course, the grid may be designed with other geographic shapes if necessary. Such a holey carbon grid is well known in the art and includes, among other things, a perforated copper disc having a carbon layer, approximately 200 nm in thickness, extending across holes 131. The carbon layer, in an embodiment, is provided to decrease the diameter of the holes 131 on the grid 13, and does not completely cover these holes 131. In accordance with an embodiment, the holes 131 may be provided with a diameter ranging from about 1 micrometer to about 10 micrometers. In this manner, when the sample is deposited onto the grid 13, a thin film of the sample may be generated across the reduced-size holes 131. To facilitate the generation of the thin film, the CEVS 10 may be provided with a blotter 14 adjacent the grid 13 to blot excess amount of the deposited sample from the surface of the grid 13, such that an amount sufficient for generating the thin film remains on the grid 13. In addition, to maintain the grid 13 in position during the deposition process and blotting process, a plunging mechanism 15 may be provided to which the grid 13 may be affixed.

The CEVS 10 may further include a portal 16 through which the plunging mechanism 15 may extend, so as to push the grid 13 from within the CVES 10, as illustrated in FIG. 1B. In this manner the grid 13 may be immersed within a cryogenic reservoir 17 situated in proximity to the portal 16. The reservoir 17, in one embodiment, includes an inner chamber 171 within which a volume of a first cryogenic fluid may be accommodated and into which the grid 13 along with the sample may be immersed. In one embodiment, the first cryogenic fluid may be liquid ethane, or similarly cold cryogenic fluid, such as liquid propane. For ethane, the normal melting point is about −183° C., while the normal boiling point is about −89° C. The reservoir 17 may also include an outer chamber 172 situated about the inner chamber 171 for accommodating a volume of a second cryogenic fluid, such as liquid nitrogen, or a similarly cold cryogenic fluid. By positioning outer chamber 172 about inner chamber 171, the volume of liquid ethane in inner chamber 171 may be kept sufficiently cold and substantially close to its melting point by the presence of the liquid nitrogen in the outer chamber 172 to maximize heat transfer away from the sample and to allow the sample to vitrify rather than crystalize. The reservoir 17 may further include a grid holder 18 submerged within the liquid nitrogen in the outer chamber 172 for subsequent placement of the grid 13 thereon.

2. Preparation of the Sample

Still looking at FIGS. 1A-C, approximately 1-10 microliters of the liquid sample may be withdrawn from vial 11 using pipette 12, and subsequently deposited onto perforated grid 13. In one embodiment, the sample may be about 2-5 microliters in volume, and preferably, about 3 microliters in volume. The sample may thereafter be blotted by blotter 14, so as to leave on grid 13 a thin film having a thickness ranging from about 50 nm to about 200 nm spanning the holes 131. It should be noted that thickness of the thin film may not be substantially uniform throughout. To that end, areas of the film that is relatively thin can provide an ideal location for imaging.

The sample on grid 13 may then be immersed by plunging mechanism 15 into reservoir 17, as shown in FIG. 1B, and in particular, into chamber 171 of liquid ethane having a temperature range of from about −170° C. to about −150° C. As noted above, the liquid ethane may be kept close to its melting point by the liquid nitrogen in the outer chamber 172 to maximize heat transfer from the grid. Contact of the sample on the grid 13 with the liquid ethane in chamber 171 can induce rapid vitrification of the sample on grid 13 within a few milliseconds. It should be appreciated that during vitrification, liquid, such as water, in the solution solidifies without crystallization. In this manner, substantially all of the microstructures in the sample may be preserved in their original state. The grid 13 may next be transferred from the inner chamber 171 of the reservoir 17 to the outer chamber 172 and placed onto the grid holder 18 in liquid nitrogen.

Referring now to FIG. 2, the grid 13 may thereafter be transferred from the holder 18 onto a cold stage 20 in the liquid nitrogen environment of the outer chamber 172 of reservoir 17. Transferring the grid 13 in a liquid nitrogen environment can help to maintain the integrity of the sample. As illustrated, cold stage 20 may include a container 21 within which a volume of, for instance, liquid nitrogen or any other similarly cold substance may be stored, and an arm 22 extending from the container 21. Arm 22, in an embodiment, may be designed for placement within the liquid nitrogen environment of the outer chamber 172, and may be tubular in shape. As such, arm 22 may be made from a material that can withstand immersion in liquid nitrogen. Arm 22 may also include a channel 23, so as to permit liquid nitrogen from container 21 to advance to tip 24 and maintain the temperature of the arm 22 thereat from about −170° C. to about −160° C., substantially well below the amorphous to crystalline phase transition temperature of about −155° C. in ice, to minimize any compromise to the integrity of the sample. As shown in FIG. 2, arm 22 may include a depression 25 towards tip 24 to provide an area onto which grid 13 may be placed for subsequent imaging. Cold stage 20, in one embodiment, can be a commercially available cold stage, such as the Cryotransfer System—CT3500J from Oxford Instruments.

Once the grid 13 has been transferred onto arm 22 of cold stage 20, the cold stage 20 may be inserted into, for instance, a high contrast imager (not shown), such as a TEM, under positive dry pressure to minimize the risks of contamination of the sample by, for example, atmospheric contaminants, including moisture. The positive dry pressure may be generated from any gas, such as nitrogen or oxygen. During imaging, such as phase contrast imaging, the tip 24 of arm 22 continues to be maintained at a temperature range well below the amorphous to crystalline phase transition temperature of about −155° C. in ice, in the electron microscope to maintain the integrity of the sample being imaged.

M-FFDI Technique:

In samples having a viscosity that may be relatively high, i.e., greater than about 100 centipoise, for blotting to effectively thin down the samples, the use of cryo-TEM may not be sufficient. As such, the present invention contemplates the use of M-FFDI.

Looking now at FIG. 3, in one embodiment, approximately 100 nanoliters (nL) of the sample 30 may placed onto a plate or planchette 31. Planchette 31, in an embodiment, may be a copper planchette, or may be made from a similar material of approximately 3 mm×3 mm in size. Next, a grid 32, either standard electron microscope grid or a holey carbon grid, such as that described above, may be placed onto the planchette 31 over the sample 30, so that the sample 30 may permeate across the perforations of the grid 32. In an alternate embodiment, the sample 30 may initially be placed on the grid 32 and the grid 32 subsequently placed onto the planchette 31. The planchettes 31, in accordance with an embodiment, may be relatively larger in size than the grid 32, so as to accommodate the grid 32 thereon.

Thereafter, a second planchette 33 may be gently lowered onto the grid 32 to sandwich the grid 32 between the two planchettes 31 and 33. It should be appreciated that gentle placement of the second planchette 33 onto the grid 32 allows the sample 30 to be squeezed between the planchettes 31 and 33, and spread out over the surface of the grid 32 into previously unoccupied areas. Moreover, the spreading of the sample 30 across of the grid 32 into previously unoccupied areas generates certain thin film portions that can be substantially thinner in thickness than others across the perforations of the grid 32. The presence of the relatively thin portions can facilitate imaging of the structures within these thin portions of the sample 30.

The planchette-grid-planchette sandwich may then be immersed into, for instance, liquid ethane that is maintained near its melting point with a temperature range of from about −170° C. to about −160° C. Once vitrification of the sample 30 has taken place, the copper planchettes 31 and 33 may be separated (e.g., peeled apart) while they remain immersed in the liquid ethane to remove the grid 32 therebetween. In an embodiment, a cryogenically cooled forceps (not shown) may be used to separate the grid 32 from the two planchettes. Next, the grid 32 may be withdrawn and stored under liquid nitrogen, for instance, on a grid holder, such as that shown in FIG. 1B, until it is ready to be transferred to cold stage 34 for direct imaging of the ultrastructural biomarkers within the sample 30.

This technique can be suited for preparation of highly viscous samples and gels, where blotting may not be feasible, for subsequent high resolution imaging. In other words, those samples that cannot be prepared for imaging using cryo-TEM can be prepared using this M-FFDI technique. This technique can also be employed to prepare samples that have a predominant organic phase that tend to dissolve if exposed directly to ethane. Accordingly, by providing these two approaches for imaging, a substantially complete range of solutions or biological fluids that can be imaged.

The combination of cryogenic vitrification for sample preparation and the high contrast microscopy for imaging of the sample can produce reliable, substantially artifact-free direct images of ultrastructural biomarkers, for instance, nanoscale aggregates in solution, or of soft tissue sections in their native states. It should be appreciated that neither cryo-TEM nor M-FFDI requires the use heavy metal salts to create contrast, thus avoiding salt-related phase transitions. In addition, the structural information obtained from cryo-TEM or M-FFDI, when applied to, for instance, computer based reconstruction of images obtained at different angles or stage tilts, can provide three dimensional (3-D) structural information on macromolecular assemblies. Such 3-D reconstruction is well known in the art, for example, 3-D images created from CAT scans.

Although the use of cryogenic vitrification is described above in connection with cryo-TEM and M-FFDI, it should be appreciated that such can be employed with other imaging approaches. For instance, cryogenic vitrification may be used in connection with Cryotoming to image and examine ultrastructural biomarkers in various tissue samples. As an example, a sample of about 1 mm square may be vitrified by high pressure freezing. The vitrified sample may then be positioned and secured on, for instance, a cold aluminum pin. Thereafter, a section of approximately 50 nm-100 nm may be microtomed (i.e., sliced) using a cold diamond knife. This sample may subsequently be placed on a carbon-coated electron microscope grid, and imaged at from about −170° C. to about −150° C. on a cold stage.

EXAMPLES

Figure 4:
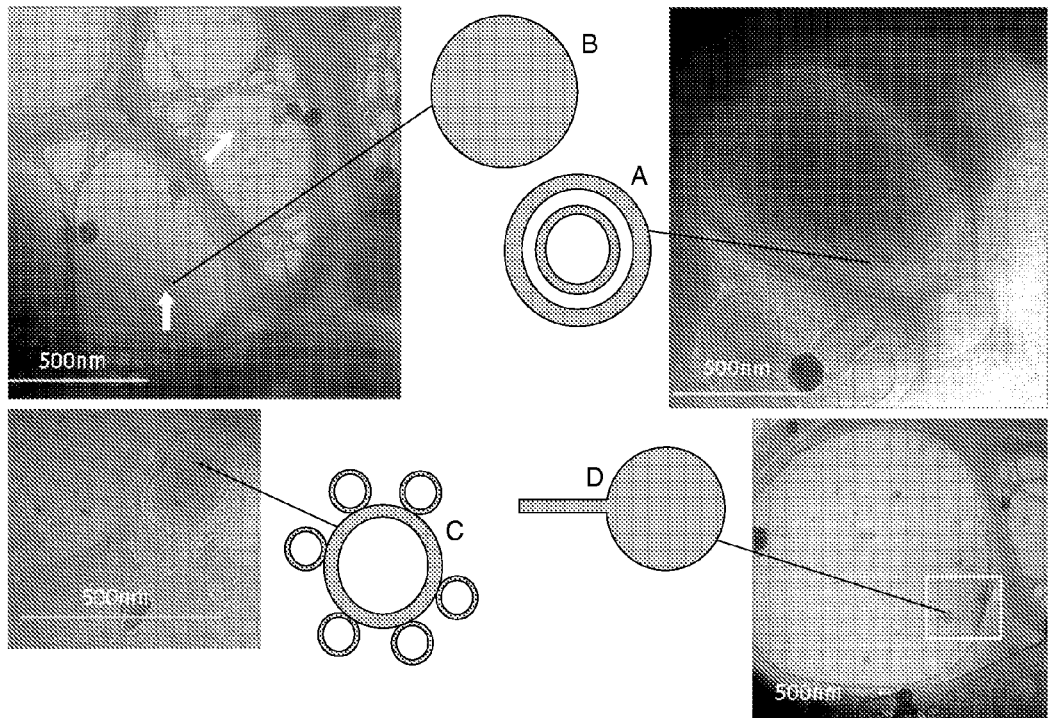
FIGS. 4A-D illustrate cryogenic TEM images of a human blood serum sample.

In an experiment, a serum sample from a test subject was prepared using cryogenic vitrification in the manner set forth above and subsequently imaged through the use of cryo-TEM. The images of the serum sample are illustrated in FIG. 4. In particular, the images are taken from different regions of the same holey carbon grid (i.e. different relatively thin regions of the thin film on the grid). As can be seen, the images show a relatively rich range of structures, including (a) multilamellar vesicles, (b) single and (d) compound discs, and (c) compound vesicles, all at nanoscale resolution of approximately 500 nm or less.

It should be noted that serum typically contains macromolecules, such as metabolites, lipids, hormones, peptides, and proteins. Certain of these biological macromolecules can also organize into 3-D complexes, which can be biochemically homogeneous or heterogenous in nature. For examples, serum can contain many glycoproteins, glycopeptides, lipoproteins, and hormones and metabolites complexed with proteins, and lipids.

Figure 5A:
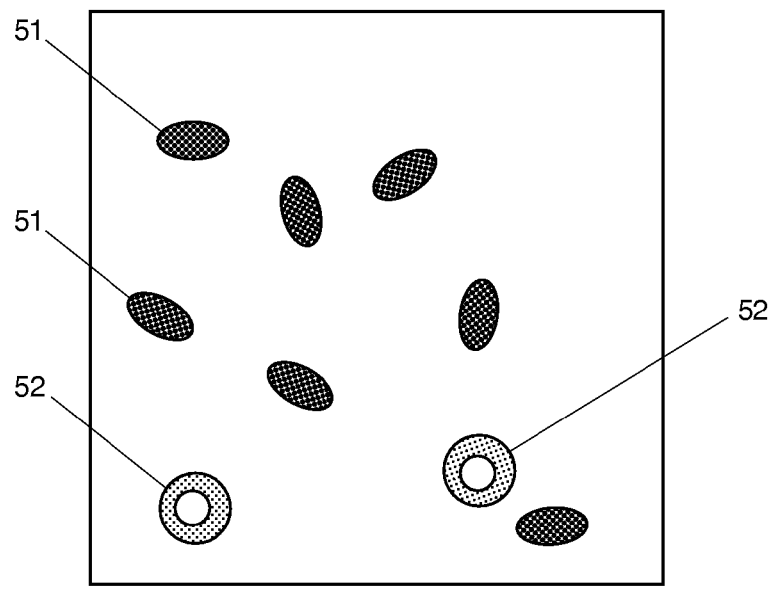
FIGS. 5A-B illustrate a change comparison in morphology and aggregate state between a control sample and a diseased sample.
Figure 5B:
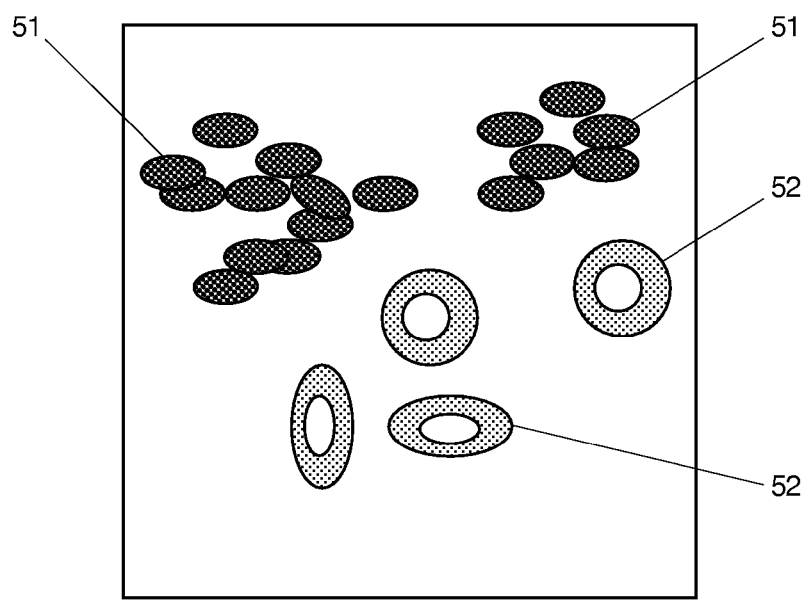

In FIGS. 5A-B, there is illustrated a comparison of the structural and physical changes between a control sample (FIG. 5A) and a diseased sample (FIG. 5B). Images of both can, of course, be obtained using the protocol set forth above. It is noted that protein structures 51 in the control sample can become more aggregated in the diseased sample, whereas vesicles 52 in the control sample can change shape, becoming more elliptical or larger in size. These structural or morphological changes can act as determinants, among other things, screening and monitoring diseases.

Other Applications

In accordance with an embodiment of the present invention, ultrastructural biomarkers identified through the use of cryo-TEM or M-FFDI may be used for a wide variety of applications, for example, to make early disease screening (i.e., prediction, susceptibility), disease monitoring, early markers of drug related toxicity, and drug efficacy, among others. Other applications that can be imagined include those for diagnostic, therapeutic, prophylactic, drug discovery, and patient stratification purposes.

A biomarker or biological marker is defined by the FDA as a characteristic that is objectively measured and evaluated as an indicator of normal biologic or pathogenic processes or pharmacological responses to a therapeutic intervention.

In diseased individuals, the composition of, for instance, serum components can be altered due to cell proliferation, metabolic, hormonal, inflammatory or secretory changes, thus impacting the structure and morphology of the resulting imaged components. As there are numerous diseases where ultrastructural abnormalities occur in cell organelles, tissue structures, and biological fluids, the utilization of ultrastructural analysis of components therein can reveal critical biomarkers associated with these diseases. Moreover, by screening and comparing biomarkers from a sample of a test subject to those biomarkers from a healthy subject or control population for structural or morphological variations, the presence of variations in the ultrastructural biomarkers from the test subject sample, in one embodiment, can act as determinants or predictors of disease, disease predisposition, and disease susceptibility.

Examples of biological fluids from which ultrastructural abnormalities can be observed include, but are not limited to blood, mucosa, plasma, serum, cerebral spinal fluid, spinal fluid, joint fluid, urine, saliva, bile, pancreatic fluid, peritoneal fluid, lung fluid, alveolar sac fluid, sinus fluid, lachrymal fluid, nasal mucous and fluid, intrathoracic fluid, gastric fluid, gastrointestinal fluid, ovarian fluid, testicular, prostrate fluid, uterine fluid, cystic fluid, renal fluid, brain fluid, opthalmic fluid, tear, ear fluid, auditory canal fluid, subcutaneous or muscular fluid.

Examples of cell organelles and tissue structures within which ultrastructural abnormalities can occur include plasma membrane, organelle membranes, basement membrane, extracellular matrix, intercellular organelles, intercellular structures, intracellular membranes, intracellular organelles, cell-cell junctions, cell-cell adhesion, gap junctions, tight junctions, nucleus, nucleolus, nuclear membrane, nuclear pore, chromosomes, chromatin, ribosomes, polyribosomes, monosomes, cellular proteins, cellular protein complexes, cellular protein subunits, extracellular proteins, extracellular protein complexes, extracellular protein subunits, secretory proteins, secreted protein complexes, secretory protein subunits, secreted intracellular or extracellular protein aggregates, golgi, lysosomes, mitochrondria, endosomes, mitochrondrial membranes, peroxisomes, endoplasmic reticulum, mRNA, DNA, tRNA, rRNA, small RNA, proteosomes, vacuoles, intracellular and extracellular vesicles, cavity, and droplets, cellular lipids or carbohydrates, cellular lipid or carbohydrate complexes, cellular lipoproteins, cellular glycoproteins, intracellular and extracellular lipids, extracellular lipoprotein complexes, extracellular lipoprotein subunits, secreted proteins, secreted protein subunits, lipoprotein or glycoprotein aggregates can reveal critical biomarkers associated with these diseases.

Moreover, it is well established that structural and morphological variations in secreted components of biological fluids, such as serum, precede or occur simultaneously with functional changes. Accordingly, the ability to monitor the structural or morphological changes in aggregates present in biological fluids in their native, hydrated states at nanoscale resolution, and which can be correlated to functional and phenotypic changes has the potential for early and simple detection of disease, classification of disease sub-categories, and monitoring of disease progression. In one embodiment, to effectively monitor the progress of a disease via an image-based platform, such as that employed in the present invention, an accurate, precise and temporally contiguous picture of the progress of the disease is needed. The method of the present invention can provide an accurate and precise image of the ultrastructural biomarkers from samples taken from a subject over a period of time. As a result, these images may be compared against one another for any structural or morphological changes in the biomarkers being observed to determine and monitor the progression of the disease.

The ultrastructural biomarkers identified can also be employed for drug or biological therapeutics screening. For example, in cell-based or in vitro drug screening, any intracellular or extracellular markers of change can be detected and utilized as a marker of drug or therapeutic efficacy or an indicator that the drug target is being hit. In particular, in one embodiment, different drugs, candidate drugs or therapeutics may be administered to test subjects, and the side effects, including desired effects, toxicity, adverse effects or serious adverse effects, may be documented. Any conventional metrics of side effect severity can be used. In addition, before and after drug administration, the biomarkers may be identified and analyzed to determine which of the biomarkers has changed. In this way, the biomarkers affected by each drug can be correlated with the particular desirable and undesirable effects of the drug.

It is anticipated that new drugs being developed will have fewer adverse effects due to extensive use of biomarkers to identify adverse events in preclinical animal models or in clinical trial patients. As additional generations of drugs continues to be developed, the list of relevant biomarkers and their changes can be refined further. In addition, as it becomes clear whether each biomarker is indicative of desired or undesired effects, more information about the mechanisms of drug action are learned, helping to direct development of next generation drugs. Accordingly, these ultrastructural biomarkers can allow for the monitoring and evaluating of drug or therapeutic safety and efficacy during discovery, preclinical and all levels of clinical trials, as well as post sales monitoring and testing. Furthermore, a similar approach may be used to determine and evaluate patient response or response rate, as well as clinical trial participant response or response rate.

Similarly, the above protocol can be employed to generate information that can lead to the understanding of the risks of adverse events, toxicity or serious adverse events associated with marketed drugs or therapeutics, drug or therapeutic candidates, as well as risks for drug attrition. Such an understanding can assist in a decision making process during clinical development, thereby driving informed stop/go decisions early in, or prior to clinical development. The information may also be used, in an embodiment, in designing and developing drugs or therapeutics that can be tailored to address only relevant disease mechanisms while causing fewer adverse effects.

The present invention, in addition to being able to resolve ultra-structural features in the morphology of cells, cellular organelles, and extracellular matrix, can also employ Cryo-TEM and M-FFDI to detect macromolecular structural differences in lipid droplets, vesicles, and other structural components in biological fluids.

Furthermore, the present invention permits, in an embodiment, identification of the spatial positions of proteins in a larger assembly or changes of protein complex morphology. This is important because proper assembly can be critical to the functioning of the protein complexes and cell organelles. In particular, there are potential changes in morphology and aggregates in different stages of disease which can change size or size distribution. Since these changes are physical, the identification process employed by a method of the present invention does not require any a priori knowledge of specific biological targets. Accordingly, sole reliance on biochemical assays can be eliminated.

The high resolution images of these ultrastructures, ranging from nanometers to micrometers in size, thus provide clear indications that cryogenic vitrification and high contrast imaging achieved through cryo-TEM or M-FFDI can generate a powerful tool for analyzing these nanostructures and changes to these nanostructures in biological samples. Whether, the sample is fluid or viscous, the provision of the either cryo-TEM or M-FFDI, as disclosed herein, can create broad capability to examine relevant bio-samples under conditions that most closely resemble their native states. For instance, biomarkers that are from any of parts of the human body, including any viruses, bacteria or other pathogens residing in any part of the human body can be identified employing the methods of the present invention.

Moreover, since the present invention involves utilization of resolutions relatively far beyond those traditionally used, the potential for discovery of early changes of structural markers can be substantially high. Thus, the use of cryo-TEM and M-FFDI coupled with image analysis can provide a novel and high resolution approach for the identification of ultrastructural biomarkers. Furthermore, such an approach has the potential to change the paradigm and dramatically reduce the cost associated with biomarker discovery and validation, by providing a robust and relatively sensitive approach to diagnosing and monitoring diseases, while simultaneously reducing drug development costs.

Although the above description has been provided in the context of human subjects, it can be equally well applied to animal models, particularly those with immune systems similar to the human immune systems. For instance, suitable animals include mice, rats, and rabbits.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A method for identifying ultrastructural biomarkers from a biological sample, the method comprising:
   providing a substantially thin film of a biological fluid sample to be imaged;
   immersing the sample in a cryogenic fluid so as to cause the sample to vitrify;
   transferring the sample onto a stage for placement in a high contrast imager;
   generating, from a high contrast imager, an image from a region of the thin film sample for subsequent identification of ultrastructural biomarkers; and
   identifying ultrastructural biomarkers in the image.

2. A method as set forth in claim 1, wherein the step of providing includes using a sample approximately 1-10 microliters in volume.

3. A method as set forth in claim 1, wherein the step of providing includes blotting the sample, so as to enhance generation of the thin film.

4. A method as set forth in claim 3, wherein, in the step of blotting, the thin film has a thickness ranging from about 50 nm to about 200 nm.

5. A method as set forth in claim 1, wherein the step of providing includes sandwiching the sample between a pair of plates, so as to generate certain portions of the sample that can be substantially thinner in thickness than others.

6. A method as set forth in claim 5, wherein, in the step of sandwiching, the thickness of the sample ranges from about 50 nm to about 200 nm.

7. A method as set forth in claim 5, further including, prior to the step of transferring, separating the plates from the sample.

8. A method as set forth in claim 7, wherein the step of separating includes using a cryogenically cooled forceps to separate the plates from the sample.

9. A method as set forth in claim 1, wherein the step of immersing includes maintaining the sample in the cryogenic fluid having a temperature range of from about −170° C. to about −150° C.

10. A method as set forth in claim 1, wherein the step of transferring includes maintaining the sample at a temperature range of from about −170° C. to about −150° C.

11. A method as set forth in claim 1, wherein the step of generating includes producing a substantially artifact-free image in the absence of contrasting agents.

12. A method for screening, monitoring, predicting or assessing susceptibility to a disease, the method comprising:
providing a vitrified biological fluid sample from a test subject;
generating, in a high contrast imager, an image from the vitrified sample for subsequent identification of ultrastructural biomarkers; and
comparing the biomarkers from the vitrified sample to those biomarkers from a healthy subject or control population for structural or morphological variations;
wherein presence of structural or morphological variations acts as determinants or predictors for a disease.

13. A method as set forth in claim 12, wherein, in the step of providing, the biomarkers are from biological fluid sample.

14. A method as set forth in claim 13, wherein the biological fluids includes one of blood, mucosa, plasma, serum, cerebral spinal fluid, spinal fluid, joint fluid, urine, saliva, bile, pancreatic fluid, peritoneal fluid, lung fluid, alveolar sac fluid, sinus fluid, lachrymal fluid, nasal mucous and fluid, intrathoracic fluid, gastric fluid, gastrointestinal fluid, ovarian fluid, testicular fluid, prostrate fluid, uterine fluid, cystic fluid, renal fluid, brain fluid, opthalmic fluid, tear, ear fluid, auditory canal fluid, subcutaneous or muscular fluid.

15. A method as set forth in claim 12, wherein, in the step of providing, the biomarkers are from cellular organelles or components, or tissue components.

16. A method as set forth in claim 15, wherein the cellular organelles or components, or tissue components include one of plasma membrane, organelle membranes, basement membrane, extracellular matrix, intercellular organelles, intercellular structures, intracellular membranes, intracellular organelles, cell-cell junctions, cell-cell adhesion, gap junctions, tight junctions, nucleus, nucleolus, nuclear membrane, nuclear pore, chromosomes, chromatin, ribosomes, polyribosomes, monosomes, cellular proteins, cellular protein complexes, cellular protein subunits, extracellular proteins, extracellular protein complexes, extracellular protein subunits, secretory proteins, secreted protein complexes, secretory protein subunits, secreted intracellular or extracellular protein aggregates, golgi, lysosomes, mitochrondria, endosomes, mitochrondrial membranes, peroxisomes, endoplasmic reticulum, mRNA, DNA, tRNA, rRNA, small RNA, proteosomes, vacuoles, intracellular and extracellular vesicles, cavity, and droplets, cellular lipids or carbohydrates, cellular lipid or carbohydrate complexes, cellular lipoproteins, cellular glycoproteins, intracellular and extracellular lipids, extracellular lipoprotein complexes, extracellular lipoprotein subunits, secreted proteins, secreted protein subunits, lipoprotein or glycoprotein aggregates.

17. A method for evaluating or predicting therapeutic efficacy or response, the method comprising:
providing a vitrified biological fluid sample from a test subject;
generating, in a high contrast imager, an image from the vitrified sample for subsequent identification of ultrastructural biomarkers; and
comparing the biomarkers from the vitrified sample to those biomarkers from a healthy subject or control population, for structural or morphological variations; and
equating the structural or morphological variations as a marker of therapeutic efficacy.

18. A method as set forth in claim 17, wherein, in the step of providing, the biomarkers are from biological fluid sample.

19. A method as set forth in claim 17, wherein, in the step of providing, the biomarkers are from cellular organelles or components, or tissue components.

20. A method as set forth in claim 17, wherein the step of equating includes associating or correlating the structural or morphological variations as a marker of response rate in clinical trial participants, patients, or in animal models.

21. A method for assessing risks of toxicity, adverse events, or serious adverse events associated with a drug or therapeutic candidate, the method comprising:
providing a vitrified biological fluid sample from a test subject;
generating, in a high contrast imager, an image from the vitrified sample for subsequent identification of ultrastructural biomarkers; and
comparing the biomarkers from the vitrified sample to those biomarkers from a healthy subject or control population, for structural or morphological variations;
wherein presence of structural or morphological variations acts as a marker for risks for toxicity, adverse events or serious adverse events associated with the drug or therapeutic candidate.

22. A method as set forth in claim 21, wherein, in the step of providing, the biomarkers are from biological fluid sample.

23. A method as set forth in claim 21, wherein, in the step of providing, the biomarkers are from cellular organelles or components, or tissue components.

24. A method as set forth in claim 21, wherein, the step of comparing, the subject or control population includes human subjects or animal subjects.

* * * * *